(12) United States Patent
Cutshall et al.

(10) Patent No.: US 7,896,881 B2
(45) Date of Patent: Mar. 1, 2011

(54) ACETABULAR INSTRUMENT AND ASSOCIATED METHOD

(75) Inventors: Tony A. Cutshall, Warsaw, IN (US); Troy D. Martin, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 929 days.

(21) Appl. No.: 10/812,426

(22) Filed: Mar. 30, 2004

(65) Prior Publication Data

US 2005/0228390 A1    Oct. 13, 2005

(51) Int. Cl.
*A61B 17/58* (2006.01)
(52) U.S. Cl. ........................................................ 606/81
(58) Field of Classification Search ............. 606/79–82, 606/86, 86 R; 408/203.5, 216, 220, 227–229
See application file for complete search history.

(56) References Cited

U.S. PATENT DOCUMENTS

| | | | |
|---|---|---|---|
| 5,658,290 A * | 8/1997 | Lechot | 606/80 |
| 6,027,503 A * | 2/2000 | Khalili et al. | 606/81 |
| 6,027,543 A | 2/2000 | Yoshizaki et al. | |
| 6,129,732 A * | 10/2000 | Lechot | 606/80 |
| 6,443,988 B2 | 9/2002 | Felt | |
| 6,475,221 B1 * | 11/2002 | White et al. | 606/80 |
| 6,482,209 B1 | 11/2002 | Engh | |
| 6,506,000 B2 | 1/2003 | Lechot | |
| 6,540,739 B2 | 4/2003 | Lechot | |
| 6,626,947 B2 * | 9/2003 | Lester et al. | 623/22.23 |
| 7,048,740 B2 * | 5/2006 | White et al. | 606/80 |
| 2002/0099447 A1 | 7/2002 | Mears | |
| 2002/0116067 A1 | 8/2002 | Mears | |
| 2003/0028196 A1 | 2/2003 | Bonutti | |
| 2003/0078587 A1 * | 4/2003 | Lechot et al. | 606/81 |
| 2003/0220647 A1 | 11/2003 | McCallum et al. | |
| 2005/0113837 A1 * | 5/2005 | Salyer | 606/80 |

FOREIGN PATENT DOCUMENTS

| | | |
|---|---|---|
| EP | 1149 562 A2 | 10/2001 |
| WO | WO 96/39951 | 12/1996 |
| WO | WO 02/49517 A1 | 6/2002 |
| WO | WO 02/102254 A2 | 12/2002 |
| WO | WO 03/068078 A1 | 8/2003 |
| WO | WO 03/086208 A | 10/2003 |

OTHER PUBLICATIONS

European Search Report dated Jul. 27, 2005 for corresponding EP application 05251834.7.

* cited by examiner

*Primary Examiner*—Eduardo C Robert
*Assistant Examiner*—Tara R Carter

(57) ABSTRACT

An acetabular reamer is provided. The acetabular reamer includes a body having a peripheral surface. The peripheral surface is defined by a radius extending from an origin. The body defines an axis of rotation of the body. The body defines an end surface operably connected to peripheral surface of the body. The body further defines a relief surface spaced from the axis of rotation and operably connected to peripheral surface. The acetabular reamer also includes a cutter operably associated with the body for reaming a portion of the acetabulum and a support structure secured to the relief surface.

31 Claims, 16 Drawing Sheets

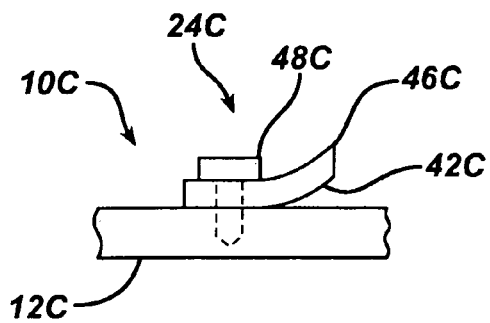
FIG. 1C
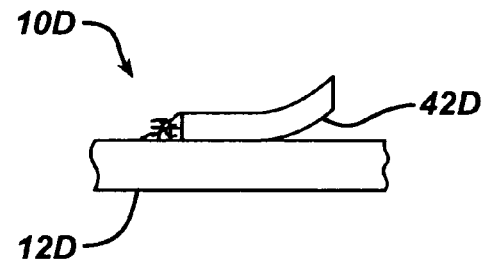
FIG. 1D
FIG. 1E
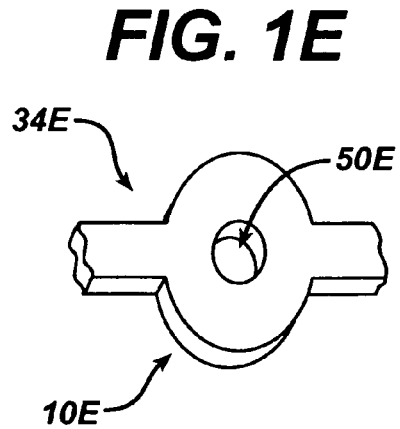
FIG. 1F
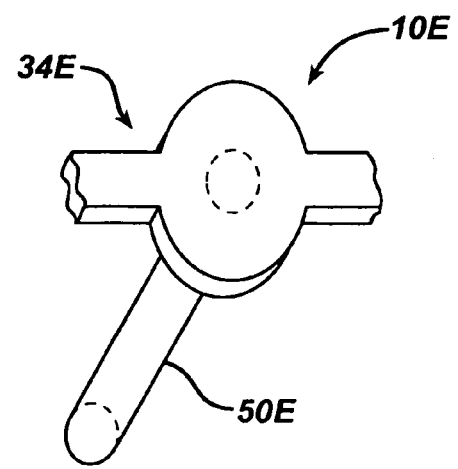

ACETABULAR INSTRUMENT AND ASSOCIATED METHOD

TECHNICAL FIELD OF THE INVENTION

The present invention relates generally to the field of orthopaedics, and more particularly, to an instrument for use in arthroplasty.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the ankle permits a hinge movement, the knee allows for a combination of gliding and hinge movements and the shoulder and hip permit movement through a ball and socket arrangement.

The joints in the body are stressed or can be damaged in a variety of ways. Gradual wear and tear is imposed on the joints through the continuous use of a joint over the years. The joints that permit motion have cartilage positioned between the bones providing lubrication to the motion and also absorbing some of the forces direct for the joint. Over time, the normal use of a joint may wear down the cartilage and bring the moving bones in a direct contact with each other. In contrast, in normal use, a trauma to a joint, such as the delivery of a large force from an automobile accident for example, may cause considerable damage to the bones, the cartilage or to other connective tissue such as tendons or ligaments.

Arthropathy, a term referring to a disease of the joint, is another way in which a joint may become damaged. One form of joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthropathy is osteonecrosis, which is caused by the death of a part of the bone due to loss of blood supply and subsequent degeneration of the cartilage. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted. The hip joint is a ball and socket joint that joins the femur or thighbone with the pelvis. The pelvis has a hemispherical socket called the acetabulum for receiving the head of the femur. Both the head of the femur and the acetabulum are coated with cartilage for allowing the femur to articulate within the pelvis. Other joints commonly afflicted include those of the spine, knee, shoulder, elbow, carpals, metacarpals, and phalanges of the hand. One means to address this affliction is arthroplasty which commonly refers to the making of an artificial joint. In severe cases of arthritis or other forms of arthropathy, such as when pain is overwhelming or when a joint has a limited range of mobility, a partial or total replacement of the joint may be justified. The procedure for replacing the joint varies, of course, with the particular joint in question, but in general involves replacing a terminal portion of an afflicted bone with a prosthetic implant and inserting a member with structural support to serve as a substitute for the cartilage.

The prosthetic implant is formed of a rigid material that becomes bonded with the bone and provides strength and rigidity to the joint and a bearing member chosen to allow for lubrication to the joint. Suitable materials for the implant include metals and composite materials such as titanium, cobalt chromium, stainless steel, ceramic and suitable materials for the bearing include polyethylene, metal and ceramics. A cement may also be used to secure the prosthetic implant to the host bone.

Total hip replacement, for example, involves removing the ball shaped head of the femur and inserting a stemmed implant into the center of the bone, which is referred to as the medullary canal of the bone. The stem implant may be cemented into the medullary canal or may have a porous coated surface for allowing the bone to heal directly to the implant. The stemmed implant has a neck and a ball shaped head, which are intended to perform the same functions as the neck and head of a healthy femur. A polyethylene, metal or ceramic liner with a metal shell is inserted into the acetabulum and acts as socket for receiving the head on the stemmed implant.

Current methods of preparing the rigid elements of a joint to receive components as in joint replacement surgery involve extensive surgical exposure. The exposure must be sufficient to permit the introduction of drills, reamers, broaches, and other instruments for cutting or removing cartilage and bone that subsequently is replaced with artificial surfaces. For total hip replacement; the acetabular articular surface and subchondral bone is removed by spherical reamers, the head is removed with an oscillating saw, and the medullary canal is shaped with broaches and the reamers.

One difficulty with total hip replacement is that the invasiveness of the procedure may cause significant blood loss and extensive rehabilitation because muscle and tendons may be released from the proximal femur to mobilize the femur and gain exposure and access to the acetabular fossa.

Conventional total hip arthoplasty is indicated for painful arthritis of the hip. The procedure involves exposing the hip joint through an incision to provide the surgeon full visualization of the hip joint and the acetabular region and to provide access for surgical power instruments. In order to appropriately prepare the bony structures of the hip joint, the major muscles spanning the joint are commonly disturbed to gain adequate exposure of the joint.

The steps of the procedure include removing the femoral head following by reaming and broaching the femoral canal to prepare the bony surface to support a hip stem. The stem is implanted and may be cemented in place or press fit for bony in-growth. The acetabulum is prepared using a hemispherical reamer to remove cartilage down to the bleeding bone. Once the acetabular surface is prepared, the acetabular component is implanted, either by cementing in place or by press fitting a metal shaft shell bony in-growth.

Surgical exposure on an incision in the skin is necessary to accommodate the bulk and geometry of the components as well as the instruments for bone preparation. The surgical exposure, which may be between six and twelve inches in length, may result in extensive trauma to the skin tissue surrounding the hip joint along with the release of muscles that insert into the proximal femur.

The surgical exposure may increases bleeding, pain, and soft tissue damage. All of these may contribute to a longer hospitalization and rehabilitation before the patient can be discharged. The bony surfaces subject to this type of surgery include but are not limited to the acetabular fossa, femoral canal, and metaphyseal/diaphyseal region of the femur. Prior to placing the final implants into the prepared spaces, a femoral trial, which may be the broach in some systems, is placed in the femur along with a trial femoral neck and head, and an acetabular trial is placed into the acetabulum to facilitate trial range of motion and to evaluate hip stability prior to placement of the final total hip implants.

For patients that require hip replacements, it is desirable to provide surgical methods and instruments that may be used to gain surgical access to the articulating joint surfaces, to appropriately prepare the bony structures, to provide artificial, articular bearing surfaces, and to close the surgical site, all without substantial damage or trauma to associate muscles, ligaments, or tendons. To obtain this goal, a system or method is needed to enable the articulating surfaces of the joint to be appropriately prepared using minimally invasive instruments and procedures.

Typical acetabular reamers are hemispherical in shape and have sharp raised portions such as that of a cheese grater. The reamers cover the majority of the acetabular surface during reaming. This enables the surgeon to adequately prepare or machine the acetabulum to accept an acetabular shell and liner during total hip arthoplasty.

As surgeons have attempted to reduce the overall size of the incision and develop less invasive procedures, access to the femur and acetabulum are reduced. A need therefore has arisen for instruments that may more easily fit into a smaller incision for use in these less invasive total hip arthoplasty procedures.

Attempts have been made to reduce the size of the acetabular reamer by simply removing material from the spherical shape. This approach, however, is not ideal in that the reamer material is somewhat thin and flexible. Simply removing the material from the hemispherical shape can lead to an inaccurate reamed shape as the reamer's surface rotates within the acetabulum.

The present invention is designed to overcome at least one of the aforementioned problems.

SUMMARY OF THE INVENTION

The current invention provides an orthopedic instrument for reaming a patient's bone to receive a prosthesis. The reaming member includes a distal arcuate region in the form of a partial sphere. The partial sphere may have an arch less than 180 degrees and may have a proximal support hub. The reaming member has an outer bone contact surface, which may include cutting teeth on at least a portion of the contact surface. The overall profile of the reamer is truncated from the hemisphere with reinforced sides to facilitate ease of insertion into the skin incision, yet provide the needed strength for reaming the acetabulum.

The present invention is in the form of a low-profile orthopedic reaming instrument for creating a new acetabular surface during total hip arthoplasty. The reamer or grater in the distal region consists of a partial sphere having an arch approximately 180 degrees and in the proximal region consisting of central support hub. The overall profile of the reamer is truncated from a full-hemisphere with reinforced sides to facilitate ease of insertion into minimal skin incisions, yet provide the strength needed for reaming the acetabulum.

According to one embodiment of the present invention, there is provided an acetabular reamer. The acetabular reamer includes a body having a peripheral surface. The peripheral surface is defined by a radius extending from an origin. The body defines an axis of rotation of the body. The body defines an end surface operably connected to the peripheral surface of the body. The body further defines a relief surface spaced from the axis of rotation and operably connected to the peripheral surface. The acetabular reamer also includes a cutter operably associated with the body for reaming a portion of the acetabulum and a support structure secured to the relief surface.

According to another embodiment of the present invention there is provided an acetabular reamer. The reamer includes a body having a peripheral surface. The peripheral surface is defined by a radius extending from an origin. The body defines an axis of rotation of the body. The body defines a generally planar end surface operably connected to the peripheral surface of the body. The end surface is perpendicular to the axis of rotation of the body. The body defines a generally planar first relief surface spaced from the axis of rotation and operably connected to the peripheral surface. The body defines a generally planar second relief surface spaced from the axis of rotation of the body and from the first relief surface. The second relief surface extends from the peripheral surface of the body. The reamer also includes a cutter operably associated with the body for reaming a portion of the acetabulum and a first support structure secured to the first relief surface. The reamer also includes a second support structure secured to the second relief surface.

According to yet another embodiment of the present invention there is provided a rotatable tool for preparing a surface of bone for implantation of a prosthesis for use in arthroplasty. The tool includes a body including a peripheral surface. The peripheral surface is defined by a radius extending from an origin. The body defines an axis of rotation of the body. The body defines an end surface operably connected to the peripheral surface of the body. The body defines a relief surface spaced from the axis of rotation of the body and operably connected to the peripheral surface. The tool further includes a cutter operably associated with the body for reaming a portion of the acetabulum and a support structure secured to the relief surface.

According to a further embodiment of the present invention, there is provided a method for implanting a prosthesis to perform joint arthroplasty on a patient. The method includes the step of providing a cutting tool including a body having a peripheral surface. The peripheral surface is defined by a radius extending from an origin. The body defines an axis of rotation of the body. The body defines an end surface operably connected to the peripheral surface. The body also defines a relief surface spaced from the axis of rotation and operably connected to the peripheral surface. A cutter is operably associated with the body for reaming a portion of the acetabulum. The body also includes a support structure secured to the relief surface. The method also includes the steps of cutting an incision in the patient and of using the cutting tool to prepare a cavity for the prosthesis. The method also includes the step of implanting the prosthesis in the patient.

The technical advantages of the present invention, include the ability for the reamer or tool to be inserted into a smaller incision into a patient and to disturb less soft tissues in its use within the patient.

Another technical advantage of the present invention includes the ability to be less invasive to the patient causing less damage to soft tissue.

For example, according to one aspect of the present invention, parallel spaced-apart surfaces are provided for a rotating acetabular reamer.

Thus the present invention provides for the use of a smaller incision and less disturbance of soft tissue, which may reduce the discomfort to the patient and patient recovery time.

Yet another technical advantage of the present invention is the ability of the acetabular reamer of the present invention to have improved rigidity and strength with a reduced cross section.

For example, according to one aspect of the present invention an acetabular reamer is provided, which includes a support positioned adjacent a relief surface of the reamer. The support surfaces add strength and structural rigidity to the acetabular reamer.

Thus the present invention provides for improved rigidity and strength of a reamer having reduced cross section.

Yet another technical advantage of the current invention is the ability of the reamer of the present invention to provide an accurate reamed shape for preparation of a cavity for inserting a prosthetic hip cup.

For example, according to one aspect of the present invention the acetabular reamer includes a peripheral surface in a generally hemispherical shape including grater type cutters, which are universally used for preparing an acetabulum.

Thus the present invention provides for an optimum arcuate cavity for a prosthetic hip cup.

The further technical advantage of the present invention includes the ability to easily clean and sterilize the cutter.

For example, according to another aspect of the present invention the acetabular reamer includes relief surfaces which provide for an open shape to the reamer to prevent the accumulation of the bone and blood in the acetabular reamer and to provide easy cleaning and sterilizing by normal sterilization methods.

Thus the present invention provides for an acetabular reamer with a shape that is easy to clean.

Another technical advantage to the present invention includes the low cost and easy manufacturability of the acetabular reamer of the present invention.

For example, according to one aspect of the present invention the acetabular reamer includes a generally, hollow hemispherical body and a formed or welded rim around the relief portion of the body. The acetabular reamer may also include a welded, unformed driver, which may be also low cost and easy to manufacture.

Thus the present invention provides a low cost, easily machined acetabular reamer.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 1C is a partial cross sectional view of an acetabular reamer in accordance with a further embodiment of the present invention having a cutter in the form of an insert attachable to the body;

FIG. 1D is a partial cross sectional view of an acetabular reamer in accordance with a further embodiment of the present invention having a cutter that is welded to the body;

FIG. 1E is a partial cross sectional view of an acetabular reamer in accordance with a further embodiment of the present invention having a drive connection including an aperture;

FIG. 1F is a partial cross sectional view of an acetabular reamer in accordance with a further embodiment of the present invention having a drive connection including a stem;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
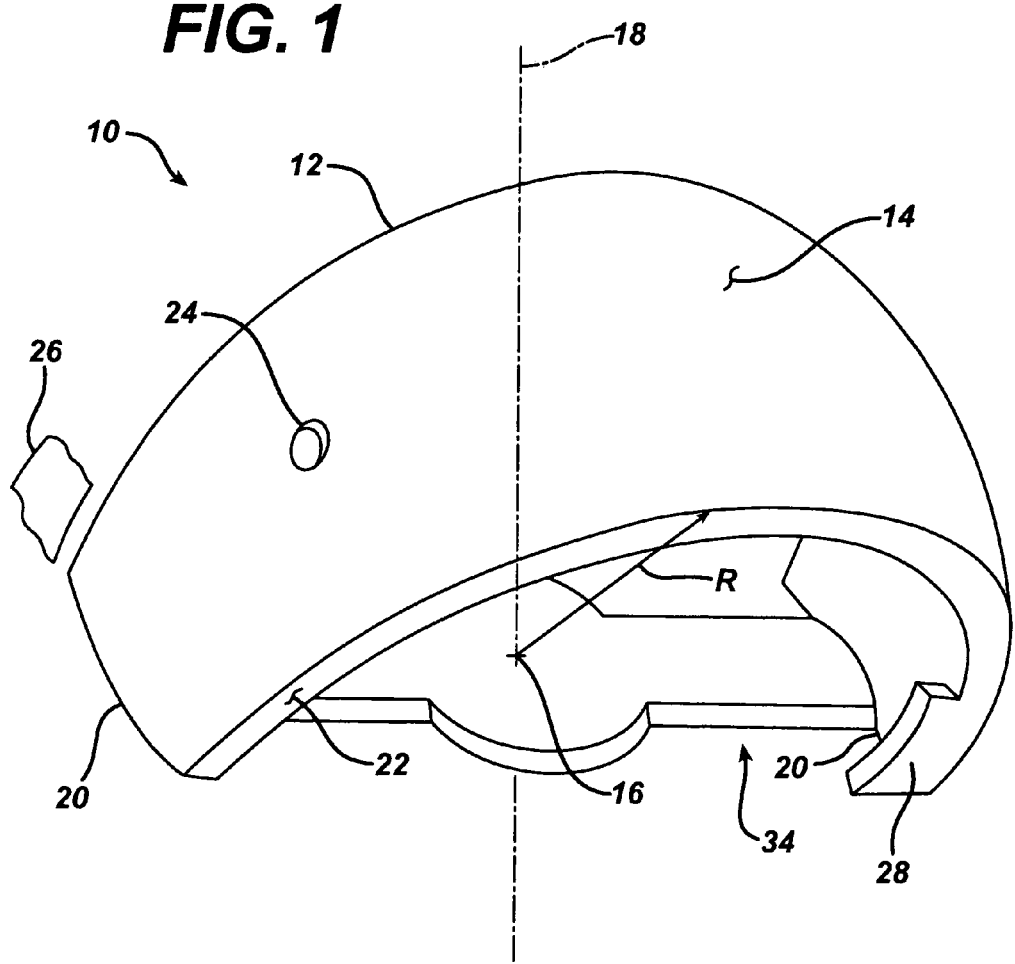
FIG. 1 is a perspective view of an acetabular reamer in accordance with an embodiment of the present invention showing.

According to the present invention, and referring now to FIG. 1, a cutting tool in the form of an acetabular reamer 10 is shown. The acetabular reamer 10 includes a body 12. The body 12 has a peripheral surface 14. The peripheral surface 14 is defined by a radius R extending from an origin 16. The body 12 defines an axis of rotation 18 of the body 12. Body 12 further defines an end surface 20 that is operably connected to the peripheral surface 14. The body 12 further defines a first relief surface 22 that is spaced from the axis 18, and that is operably connected to peripheral surface 14 of the body 12.

The acetabular reamer 10 further includes a cutter 24. The cutter 24 is operably associated with the body 12 and is utilized for reaming a portion of acetabulum 26 of the patient. The acetabular reamer 10 further includes a support structure 28, which is secured to relief section 22 of the body 12 for providing structural support to the relief surface 22 and to the body 12 in general.

The end surface 20 of the body 12 may add any suitable shape. The end surface 20 may extend inwardly from peripheral surface 14 of the body 12. The end surface 20 of the body 12 may be generally planar and may be perpendicular to the axis of rotation 18 of the body 12.

The reamer 10 may be made of any suitable material and have any shape capable of preparing the acetabulum. For example, the reamer 10 may be made of a suitable durable material, for example a metal. If made of a metal, the reamer is preferably made of material that may be sterilized by a conventional sterilizing technique such as by autoclaving. The reamer 10 may be made of one piece or may be made of an integral construction. Alternatively, the body 12, cutter 14, and the support structure 28 may each be made of a separate component which may be assembled to reamer 10. For example, the reamer 10 may be made of components and assembled by welding, brasing, or by being connected by fasteners. (not shown)

For example, shown in FIG. 1 peripheral surface 14 of the body 12 may be generally convex. For example and is shown in FIG. 1 the peripheral surface 14 may have the general form of truncated hemisphere. For example, the peripheral surface may be formed by a hollow truncated hemisphere. As is shown in FIG. 1, the peripheral surface 14 extends, for example, the end surface 20 as well as to relief surface 22.

Figure 3:
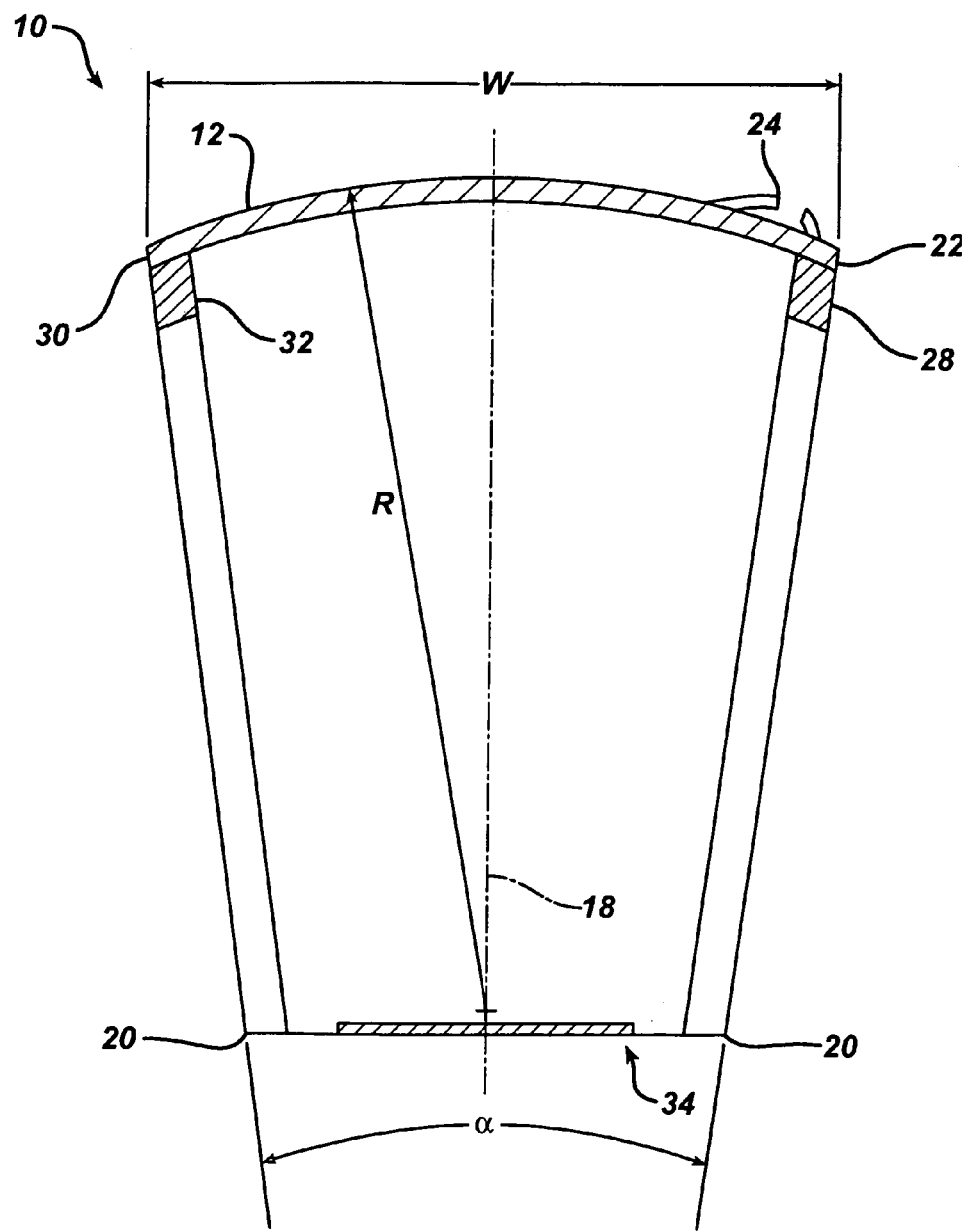
FIG. 3 is a cross sectional view of FIG. 2 along the line 3-3 in the direction of the arrows.

Referring now to FIG. 3, the acetabular reamer 10 is shown in greater detail. The body 12, as shown in FIG. 3, may define a second relief surface 30 spaced from the first relief surface 22 of the body 12. It would be appreciated that the first relief surface 22 and the second relief surface 30 of the body 12 assist in the insertion of the acetabular reamer into the body to perform less invasive surgical procedures.

The first relief surface 22 and the second relief surface 30 defined a width or distance W between the first surface 22 and the second surface 30. The distance W may for example, be less than ⅔ of the radius R of the body 12.

It should be appreciated that as the width W is reduced, a smaller incision into the patient through the skin and soft tissue could be facilitated. Thus the width W should be chosen to minimize the invasiveness of the procedure while large enough to provide for a reamer with sufficient strength and sufficient cutting surfaces to provide for a suitable surface for receiving an acetabular cup implant.

The shape of the reamer 10 may be any suitable shape to provide a sufficiently effective reamer 10. For example, and is shown in FIG. 3, the reamer 10 may have the cross sectional shape of for example, a wedge or a truss. as is shown in FIG. 3, the first relief surface 22 of the body 12 may be generally planar. Similarly, the second relief surface 30 of the body 12 may be also be generally planar. The second relief surface 30 may spaced from the first relief surface 22. The first relief surface 22 and the second relief surface 30 may define an included angle α there between. The angle α should be chosen to provide for sufficient strength to the acetabular reamer 10 while providing a sufficient cutting surface to prepare the surface of the acetabulum to provide for a proper seat for an acetabular cup implant.

As shown in FIG. 3, the acetabular reamer 10 may further include a second support structure 32 operably associated with the second relief surface 30. The second support structure 32 provides support and stability for the reamer 10, in particular for the cutter 22 located on the peripheral surface 14 of the body 12.

Figure 2:
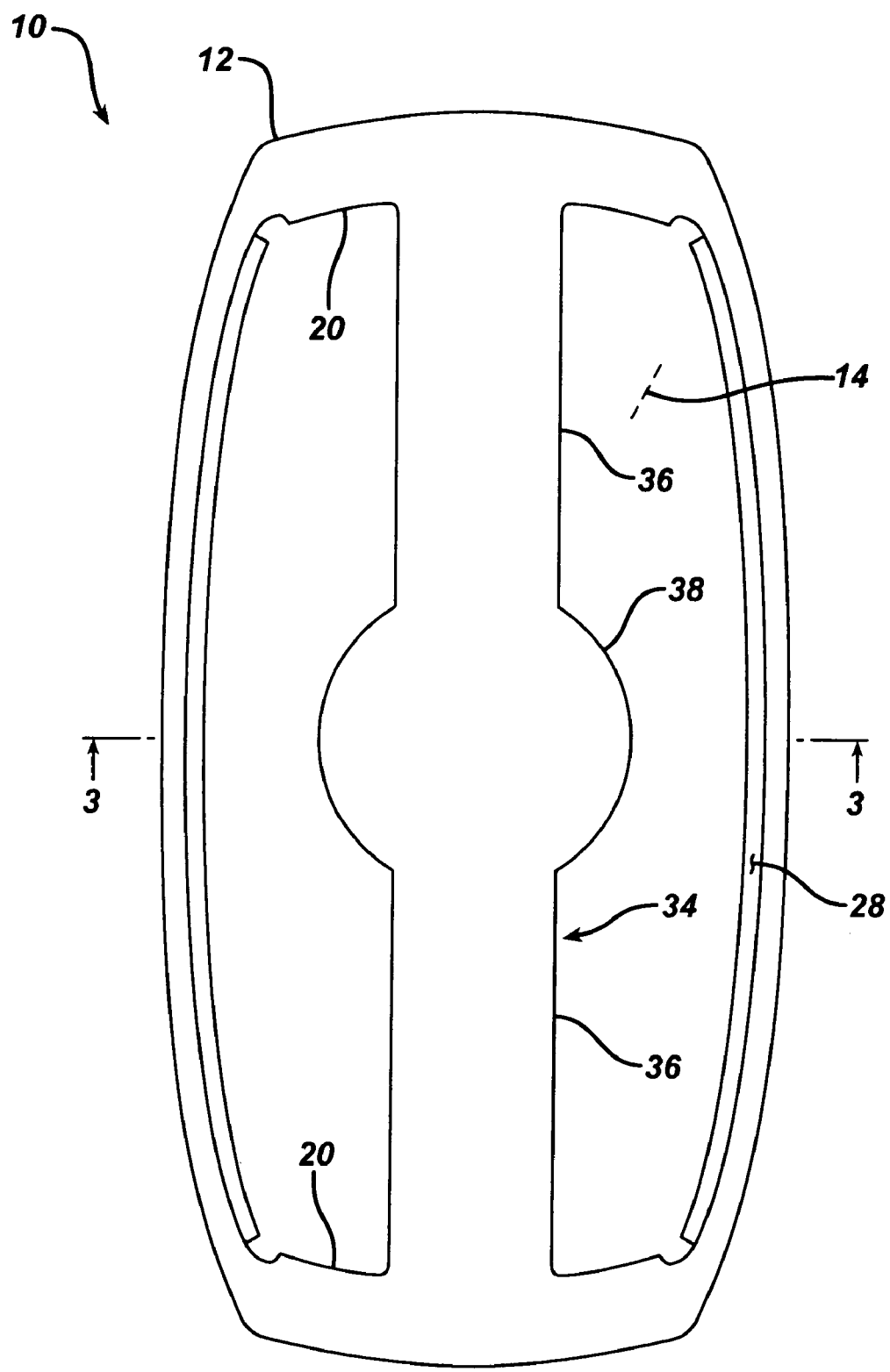
FIG. 2 is a bottom view in accordance with the embodiment of the present invention of FIG. 1.

Referring now to FIGS. 1, 2, 3, and 4 the acetabular reamer 10 of the present invention may include a driver or drive connection 34. The drive connection 34 is utilized to rotate or provide torque from a power source to the reamer 10. As is shown in FIG. 2, the drive connection 34 may be in the form of a bar extending from peripheral surface 14 of the body 12 from one of the end surfaces 20 to the other of the end surfaces 20. The drive connection 34 may include spaced apart rectangular end sections 36 and a central plate or disc shaped center portion 38.

The drive connection 34 may be integral with the body 12 of the reamer 10 or may, as shown in FIGS. 1-3, be a separate component secured to the body 12 by, for example, welding.

Referring again to FIG. 1, the cutter 24 may be any suitable cutter capable of preparing the acetabulum for the acetabular hip cup. For example, the cutter 24 as shown FIG. 1 is integral with the surface 24 of the body 12. Peripheral surface 14 is made of, for example, formed sheet metal and the cutter 24 is formed from the peripheral surface 14.

Figure 1A:
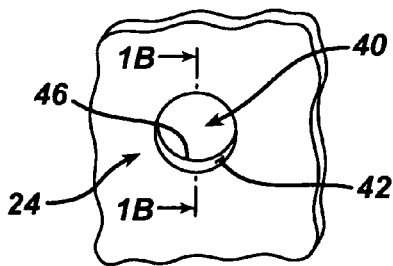
FIG. 1A is a partial perspective view of the acetabular reamer of FIG. 1 showing the cutter in greater detail.
Figure 1B:
FIG. 1B is a cross sectional view of FIG. 1 along the line 1B-1B in the direction of the arrows.

Referring now to FIGS. 1A and 1B, the cutter 24 is shown formed from an opening 40 that has a raised area or protrusion 42 is formed on a portion of the peripheral 44 formed about the opening 40. Protrusion 42 forms a cutting surface 46 for removing bone on the acetabulum. As is shown in FIG. 1, a plurality of cutters 24 may be positioned about the peripheral surface 14 of the reamer 10.

It should be appreciated that the cutter 24 may be integral of the body 12 of the reamer 10. It should be appreciated that the other configurations may equally be used in the configuration of the present invention. For example and referring now to FIG. 1C, the reamer 10c is shown having a cutter 24C. The cutter 24C is similar to the cutter 24 of FIG. 1 except that the cutter 24C includes an insert or blade 42C, which is a separate component from body 12c of the reamer 10C. A fastener 48C is utilized to secure the cutter insert 42 to the body 12.

Referring now to FIG. 1D, a reamer 10D is shown, which utilizes a separate cutter member 42D which, may be welded to body 12D of the reamer 10D.

While the drive connection 34 may be the form of a bar shown in FIG. 1 it should be appreciated that any drive connection capable of transmitting torque to the reamer 10 may be used. For example and referring now to FIG. 1E, another embodiment of the present invention is shown as a reamer 10E. Reamer 10E includes a drive connection 34E in the form of, for example, a central hole or aperture 50E. The aperture 50E may cooperate with a rod or pin on a driver (not shown).

Referring now to FIG. 1F, yet another embodiment of the present invention is shown as reamer 10F including yet another configuration of the drive connector in the form of a drive connector 34F. The drive connector 34F includes a centrally located stem 50F extending from the drive connector 34F. The stem 50F may operate with an opening or chuck (not shown) in a driver (not shown).

Figure 2A:
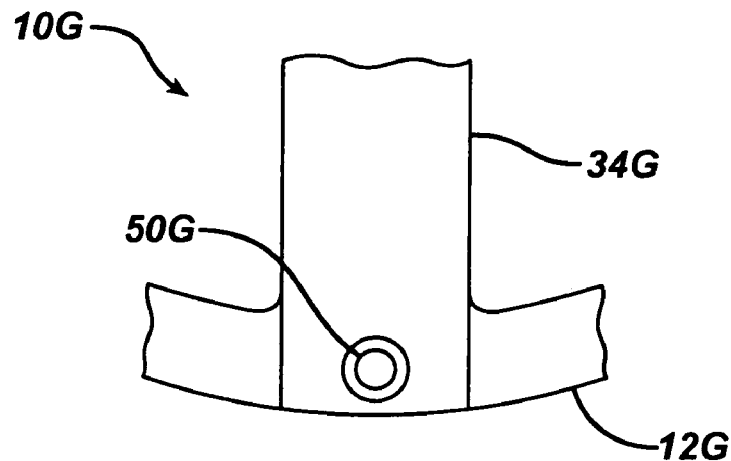
FIG. 2A is a partial cross sectional view of an acetabular reamer in accordance with a further embodiment of the present invention having a unitary drive connection.
Figure 2B:
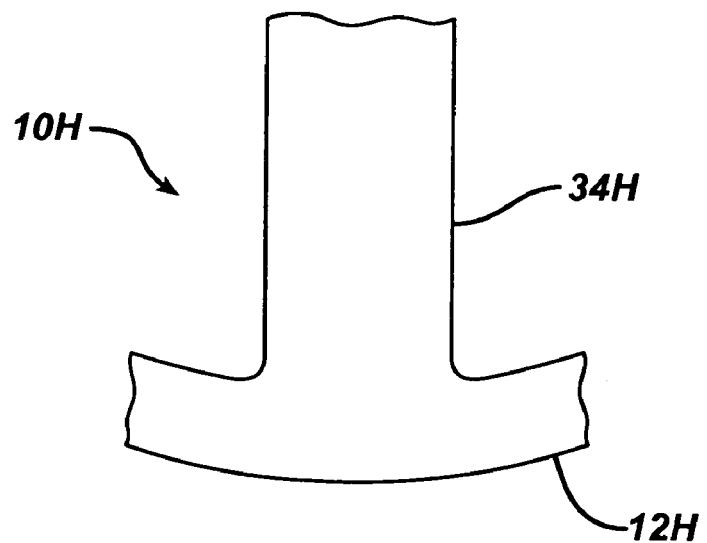
FIG. 2B is a partial cross sectional view of an acetabular reamer in accordance with a further embodiment of the present invention having a multi-piece drive connection.

It should be appreciated that the driver connector 34 of the present invention, may as shown in FIGS. 1, 2, and 3 be welded to the body 12. It should be appreciated that other constructions for the drive connection 34 may be utilized. For example and referring now to FIG. 2a, another embodiment of the present invention is shown as acetabular reamer 10G. Acetabular reamer 10G includes a drive connector 34G, which is operabley connected to the body 12G, for example by fastener 50G.

Similarly another embodiment of the present invention is shown as acetabular reamer 10H, that includes a drive connector 34H, which is integrally formed with body 12H of the reamer 10H.

Figure 5:
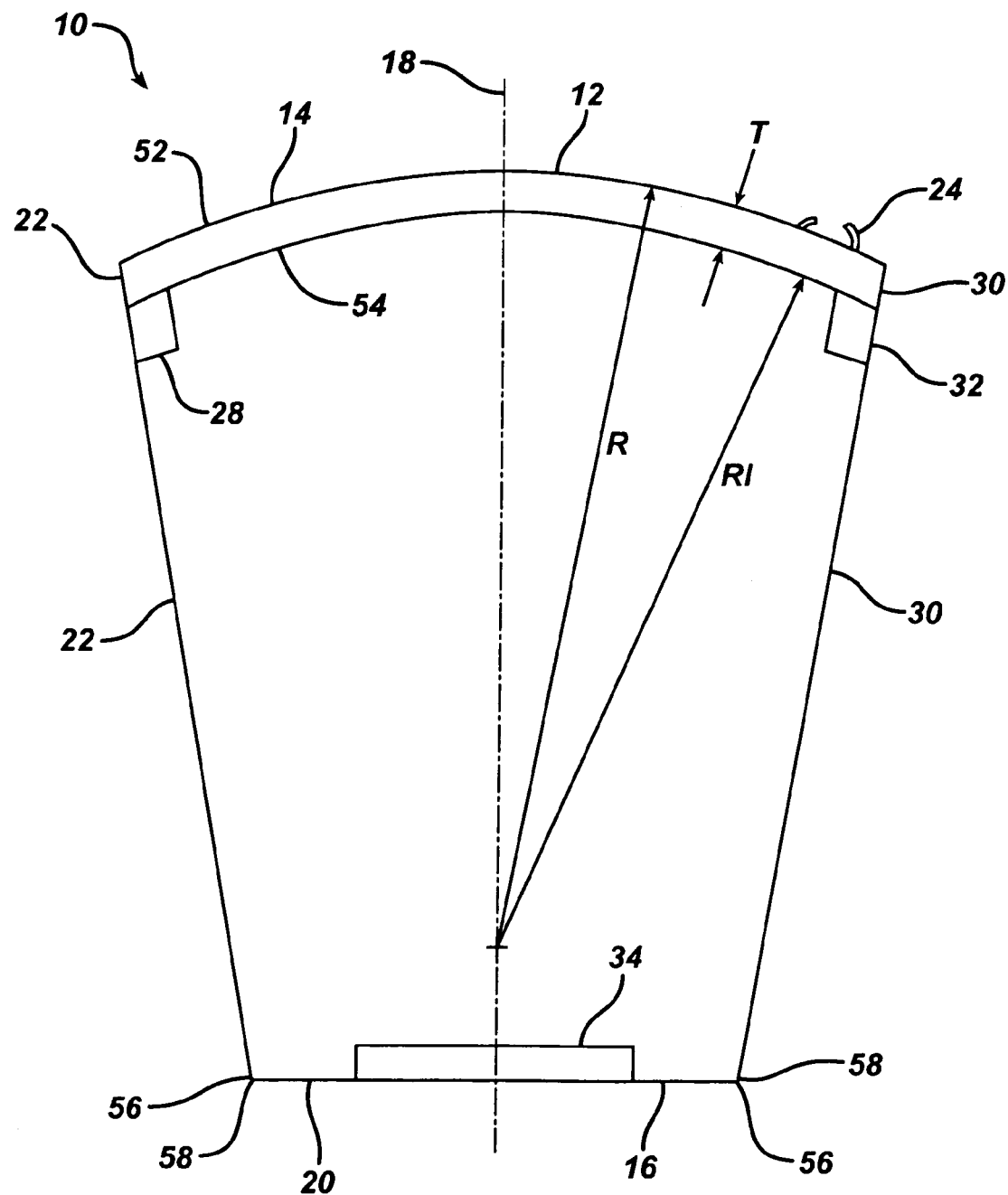
FIG. 5 is a cross sectional view of FIG. 2 along the line 3-3 in the direction of the arrows.

Referring now to FIG. 5, the acetabular reamer 10 is shown in greater detail. As shown in FIG. 5, the body 12 of the acetabular reamer 10 includes a hollow arcuate plate 52, which defines the peripheral surface 14. The plate 52 is defined by a thickness T between radius R extending from origin 16 and radius RI also extending from origin 16. To provide sufficient rigidity to the arcuate plate 52, a support structure in the form of, for example, support structure 28 it may be utilized.

As shown in FIG. 5, the support structure 28 may extend inwardly from inner face 54 of arcuate plate 52 at a position, for example, adjacent first relief surface 22 of the body 12. The first support structure 28 may, as shown in FIG. 5, have a generally rectangular cross section and extend substantially along first relief surface 22 from inner surface 54 of arcuate plate 52 to the second end surface 20 of the body 12. The support structure 28 thus has a generally rainbow-shaped construction. As shown in FIG. 5, the reamer 10 may further include a second support structure 32 likewise extending inwardly from inner articulate surface 54 of the articulate plate 52. The second support structure 32 is like the first support structure 28, may have a generally rectangular cross-section, and may extend from first end 56 to second end 58 of the end surface 20 of the body 12.

Figure 4:
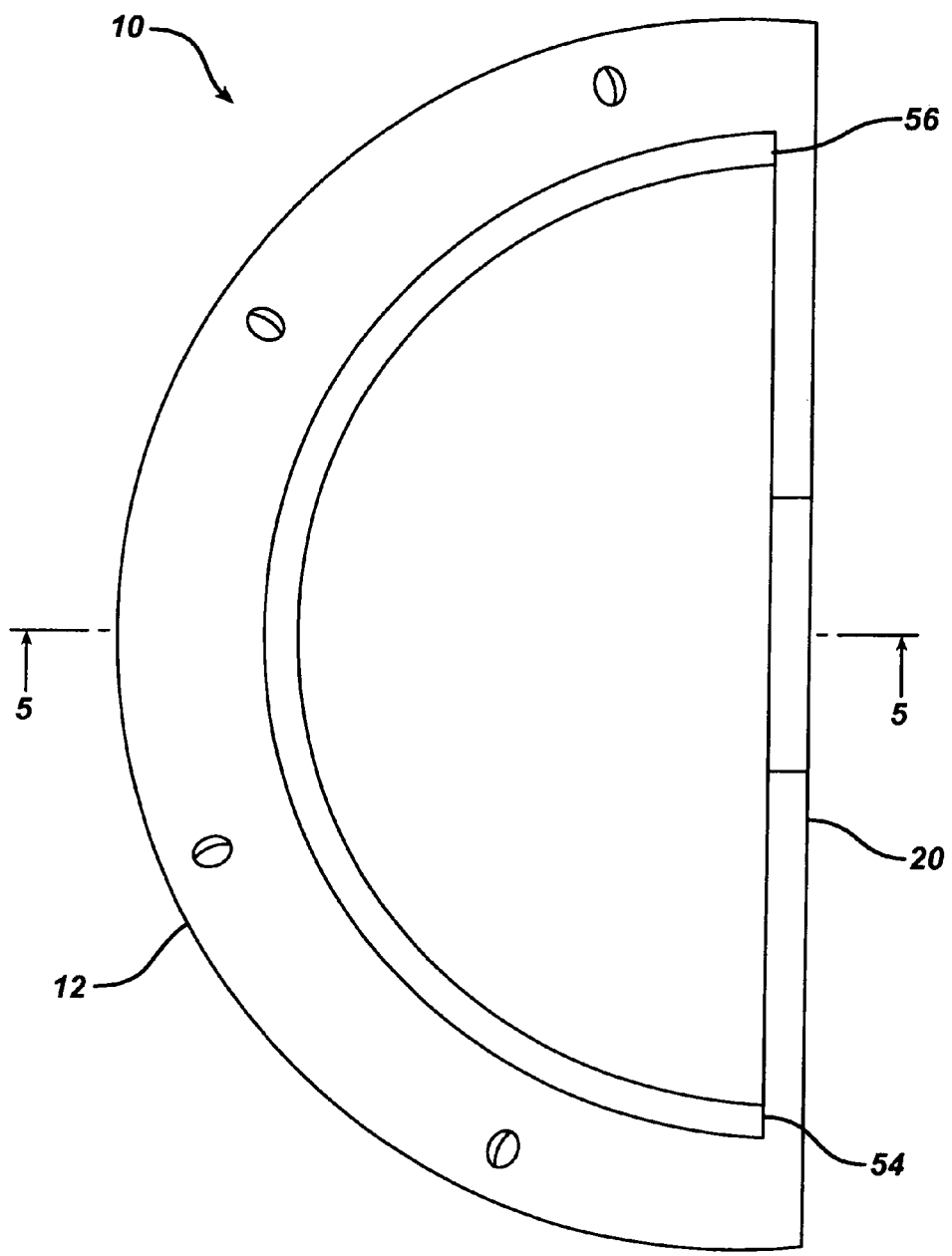
FIG. 4 is a plan view of the embodiment of the present invention of FIG. 1.
Figure 5A:
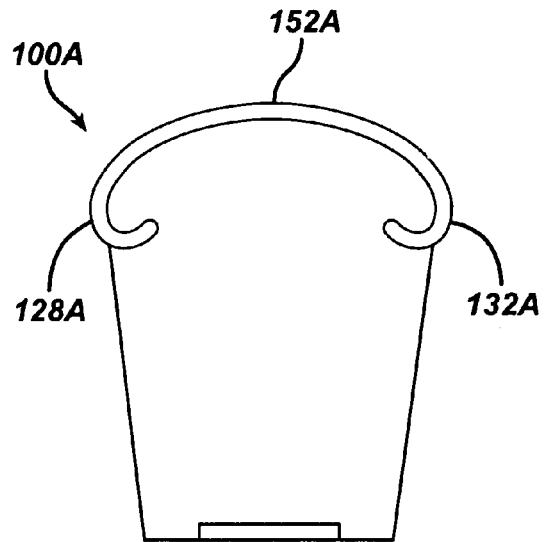
FIG. 5A is a partial cross sectional view of an acetabular reamer in accordance with another embodiment of the present invention having an alternate support structure.

Referring now to FIG. 5A, another embodiment of the present invention is shown as reamer 10A. Reamer 100A is similar to reamer 10 of FIGS. 1-5 except reamer 10A includes a first support structure 128A, which is different than the first support structure 28 of the reamer 10 of FIGS. 1-5. First support of 128A as shown in FIG. 5A, is integral with the arcuate plate of 152A and extends there from. As shown if FIG. 5A, the first support structure 128A may have an arcuate cross-section in a form of a partial loop. Reamer 101A also includes a second support structure 132A also extending inwardly from the arcuate plate 152A.

Figure 5B:
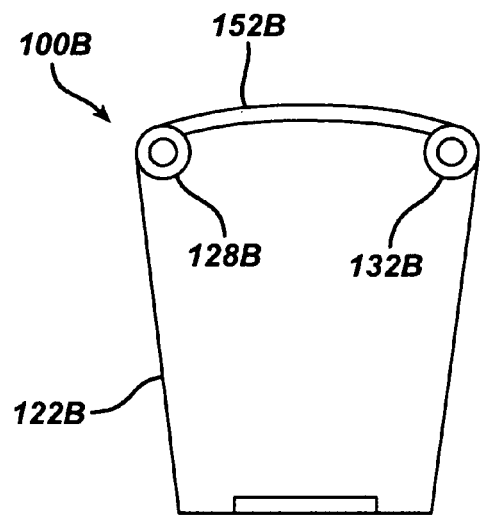
FIG. 5B is a partial cross sectional view of an acetabular reamer in accordance with yet another embodiment of the present invention having an alternate support structure.

Referring now to FIG. 5B, yet another embodiment of the present invention is shown as the acetabular reamer 100B. The reamer 100B includes a first support structure 128B, which is different than the first support structure 28 of the reamer 10 of FIG. 5. As shown in FIG. 5B, the support structure 128B is in the form of a hollow tube. The tube 128B extends from first relief surface 122B of the arcuate plate 152B of the reamer 100B. As shown in FIG. 5B, the reamer 100B includes a second support surface 132B, which is similar to the first support structure 128B and is in the form of a tube. The tubes 128B and 132B may for example, be welded to the arcuate plate 152B.

Figure 5C:
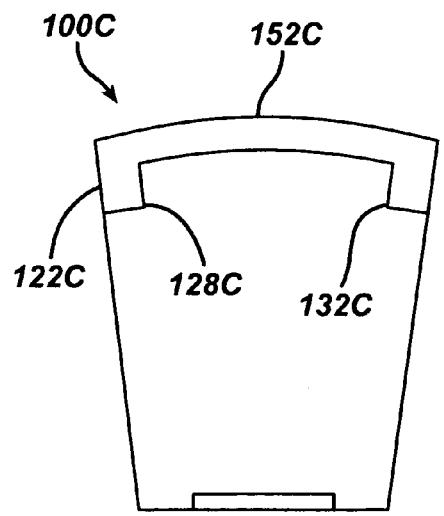
FIG. 5C is a partial cross sectional view of an acetabular reamer in accordance with another embodiment of the present invention having an alternate support structure.

Referring now to FIG. 5C, another embodiment of the present invention is shown as acetabular reamer 100C. The acetabular reamer 100C is similar to the acetabular reamer 10 of FIGS. 1-5 except that the acetabular reamer 100C has a first support surface 128C, which is different then the first support structure 28 of the reamer 10.

As shown in FIG. 5C, the first support structure 128C is in the form of an integral rib, which extends inwardly from first relief system 122C of arcuate plate 152C. Similarly, the reamer 100C includes a second support structure 132C, which is likewise integral with the arcuate plate 152C, and which extends inwardly from the plate 152C.

Figure 5D:
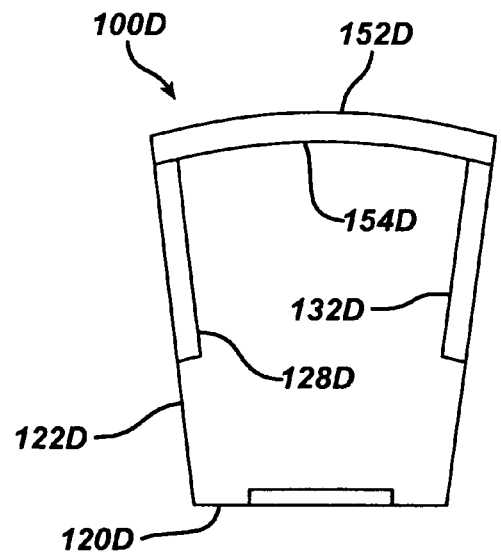
FIG. 5D is a partial cross sectional view of an acetabular reamer in accordance with yet another embodiment of the present invention having an alternate support structure.

Referring now to FIG. 5D, yet another embodiment of the present invention is shown as acetabular reamer 100D. Acetabular reamer 100D is similar to reamer 10 of FIGS. 1-5 except that acetabular reamer 100D includes a first support structure 128D, which is different from support structure 28 of the reamer 10 of FIGS. 1-5. As shown in FIG. 5D, the first support structure 128D extends inwardly from the inner articulate face 154D of arcuate plate 152D along the first relief surface 122D. The first support structure 128D as shown in FIG. 4, is in the form of a generally planar plate that extends approximately halfway between the inner articulate face 154D and end surface 120D. As shown in FIG. 5D, the reamer 100D further includes a second support surface 132D in the form of, for example, a plate similar to the plate 128D. The plates 128D and 132D may be integral with the arcuate plate 152D or as is shown in FIG. 5D, welded to the arcuate plate 52D.

Figure 5E:
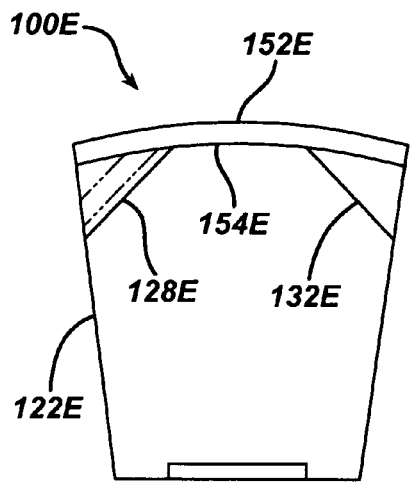
FIG. 5E is a partial cross sectional view of an acetabular reamer in accordance with a further embodiment of the present invention having an alternate support structure.

Referring now to FIG. 5E, another embodiment of the current invention is shown as acetabular reamer 100E. The acetabular reamer 100E is similar to the reamer 10 in FIGS. 1-5 except that the reamer 100E includes a first support structure 128E, which is different than the first support structure 28D of the reamer 10. For example and as shown in FIG. 5E, the first support structure 128E is in the form of a generally triangular shape gusset. The gusset 128E may be a solid angular cross gusset as shown in solid or in the form of a bar gusset that is shown in phantom. The gusset 128E extends from the inner arcuate surface 154E of the arcuate plate 152D to the first relief surface of 122E. As shown in FIG. 5E, the acetabular reamer 100E further includes a second support structure 132E in the form of a gusset.

Figure 5F:
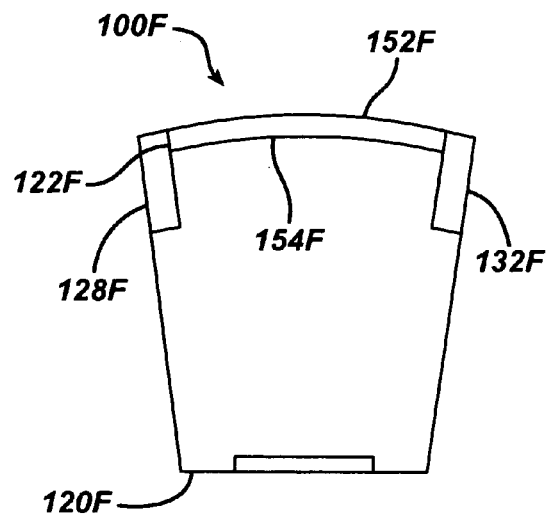
FIG. 5F is a partial cross sectional view of an acetabular reamer in accordance with another embodiment of the present invention having an alternate support structure.

Referring now to FIG. 5F, another embodiment of the present invention is shown as acetabular reamer 100F. The acetabular reamer 100F is similar to the acetabular reamer 10 of FIGS. 1-5 except that the acetabular reamer 100F of FIG. 5F includes a first support structure 128F, which is different than the first support structure 28 of the reamer 10 of FIGS. 1-5. The first support structure 128F of the reamer 10 of FIG. 5F, extends outwardly from the first end surface 122F of the arcuate plate 152F and extends inwardly past the inner arcuate surface 154F of the arcuate plate 152F. The first support structure 128F may have a generally rectangular cross section extending from surface 154F toward the end surface 120F. The acetabular reamer 100F may further include a second support structure 132F similar to the first support structure 128F.

Figure 5G:
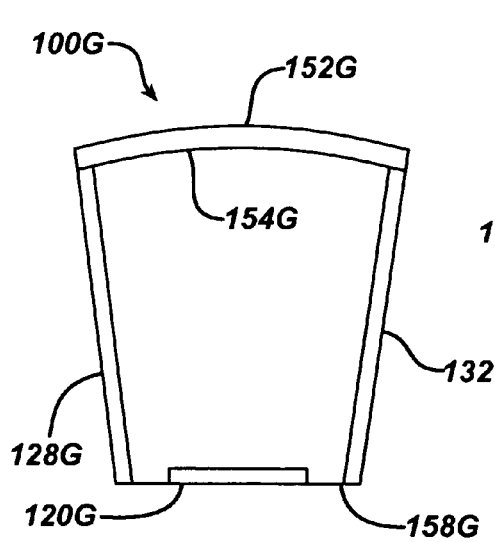
FIG. 5G is a partial cross sectional view of an acetabular reamer in accordance with yet another embodiment of the present invention having an alternate support structure.

Referring now to FIG. 5G, another embodiment of the present invention is shown as acetabular reamer 100G. The acetabular reamer 100G is similar to the acetabular reamer 10 in FIGS. 1-5, except the acetabular reamer 100G of FIG. 5G includes a first support member 128G, which is different then the first support member 28 of the reamer 10 of FIGS. 1-5. For example, referring to FIG. 5G of the first support surface 128G of the reamer 100G extends from inner arcuate surface 154G of the arcuate plate 154G to the first end 154G and second end 158G of the end surface 120G. The acetabular reamer 100G may also include a second support structure 132G in the form of a plate similar to that of the first support structure 128G.

Figure 5H:
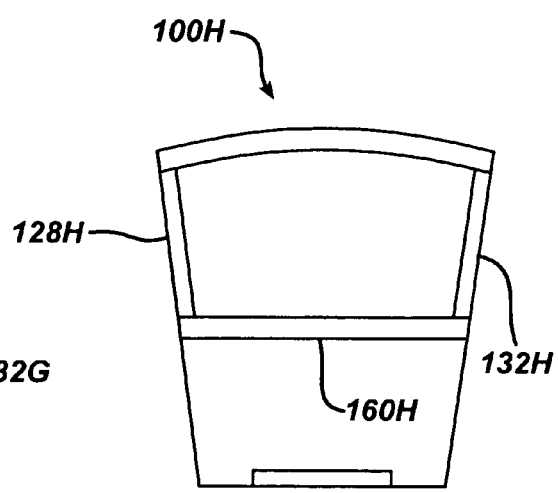
FIG. 5H is a partial cross sectional view of an acetabular reamer in accordance with yet another embodiment of the present invention having an alternate support structure.

Referring now to FIG. 5H, another embodiment of the present invention is shown as acetabular reamer 100H. The acetabular reamer 100H is similar to the acetabular reamer 10 of FIGS. 1-5 except the acetabular reamer 100H includes a third support structure 160H which extends to the proximal portion of the first support structure 100H to the second support structure 132H. The third support structure 160H provides additional rigidity to the acetabular reamer 100H.

While it can be seen that various constructions can extend from the arcuate plate of the body of the acetabular reamer to provide support, it should be appreciated that the support structure may extend on different portions or substantially all of the relief surfaces of the reamer.

Figure 5I:
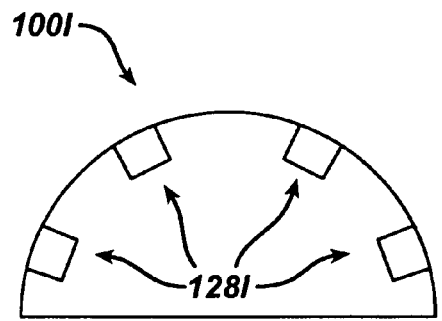
FIG. 5I is a partial cross sectional view of an acetabular reamer in accordance with a further embodiment of the present invention having an alternate support structure.

For example, and referring now to FIG. 5I, another embodiment of the invention is shown as acetabular reamer 100I. The reamer 100I of FIG. 5I is similar to the acetabular reamer 10 of FIG. 1-5 except that the first support structure 128I of the reamer 100I of FIG. 5I consists of separate spaced-apart portions, which together make the first support structure 128I.

Figure 5J:
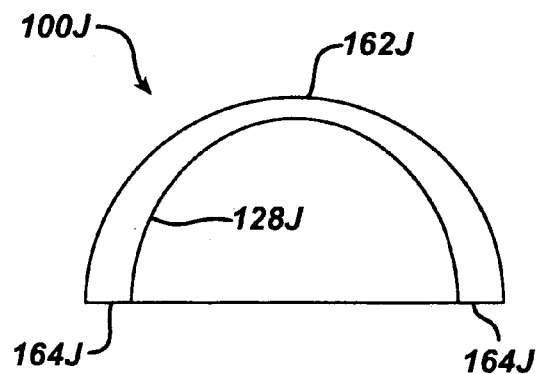
FIG. 5J is a partial cross sectional view of an acetabular reamer in accordance with yet another embodiment of the present invention having an alternate support structure.

Another embodiment of the present invention is shown in FIG. 5J as acetabular reamer 100J. The acetabular reamer 100J is similar to the acetabular reamer 10 of FIGS. 1-5 except that the acetabular reamer 100J includes a structure 128J, which is thinner in the central portion 162J of the first support structure 128J and thicker in the end portions 164J of the first support structure 128J.

Figure 5K:
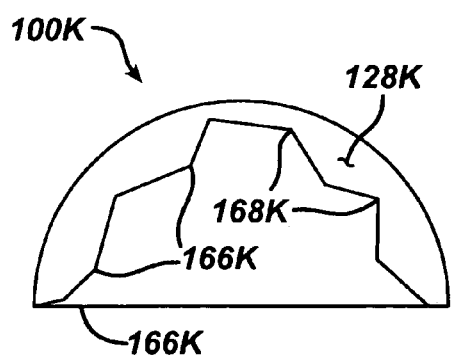
FIG. 5K is a partial cross sectional view of an acetabular reamer in accordance with a further embodiment of the present invention having an alternate support structure.

Referring now to FIG. 5K another embodiment of the present invention is shown as acetabular reamer 100K. The acetabular reamer 100K in FIG. 5K is similar to the acetabular reamer 10 of FIGS. 1-5 except that the acetabular reamer 100K includes a first support structure 128K that includes first portions 166K which are thick or extend downwardly greater than thin portions 168K of the support structure 128K which extends downwardly less then the thick portions 166K.

Figure 5L:
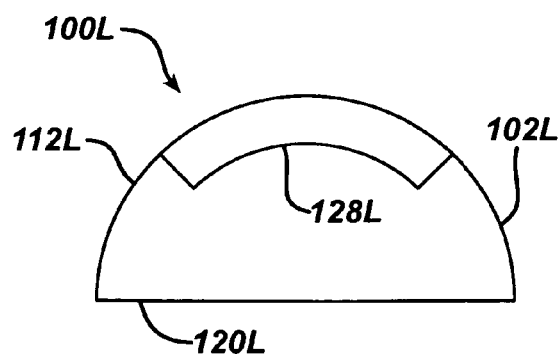
FIG. 5L is a partial cross sectional view of an acetabular reamer in accordance with a further embodiment of the present invention having yet another alternate support structure.

Referring now to FIG. 5L, another embodiment of the present invention is shown as acetabular reamer 100L. The actabular reamer 100L is similar to the acetabular reamer 10 of FIGS. 1-5 except that the acetabular reamer 100L includes a first support structure 128L, which does not extend outwardly to the end surface 120L of the body 102L of the reamer 100L.

Figure 6:
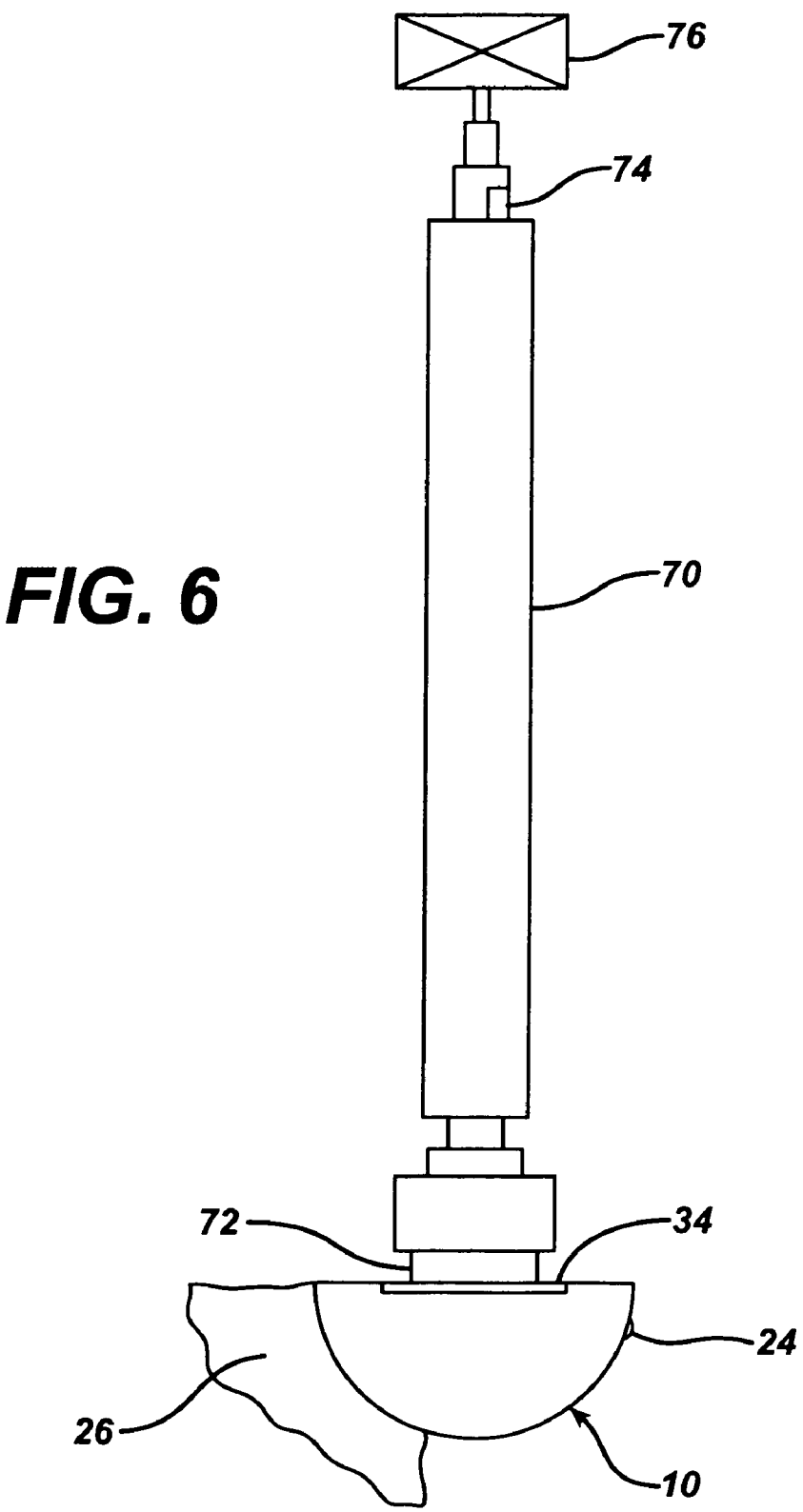
FIG. 6 is a plan view of the acetabular reamer of FIG. 1 in position on a reamer driver.

Referring now to FIG. 6 a driver 70 is shown in use with the reamer 10 in preparing the acetabulum 26. The driver 70 may be any driver capable of securely rotating the reamer 10. The driver 70 may include a reamer connection 72 for cooperating with the driver connection 34 of the reamer 10. The driver 70 may also include a connection 74 for connecting the driver 70 to the power source 76. The power source 76 may be any power source capable of rotating the reamer 10, for example, battery, pneumatic, electric, or hand power.

Driver 70 may be made of any combination of durable materials for example, plastics and metal materials, which can be preferably sterilized by commercially available sterilization techniques, such as autoclaving.

Figure 7:
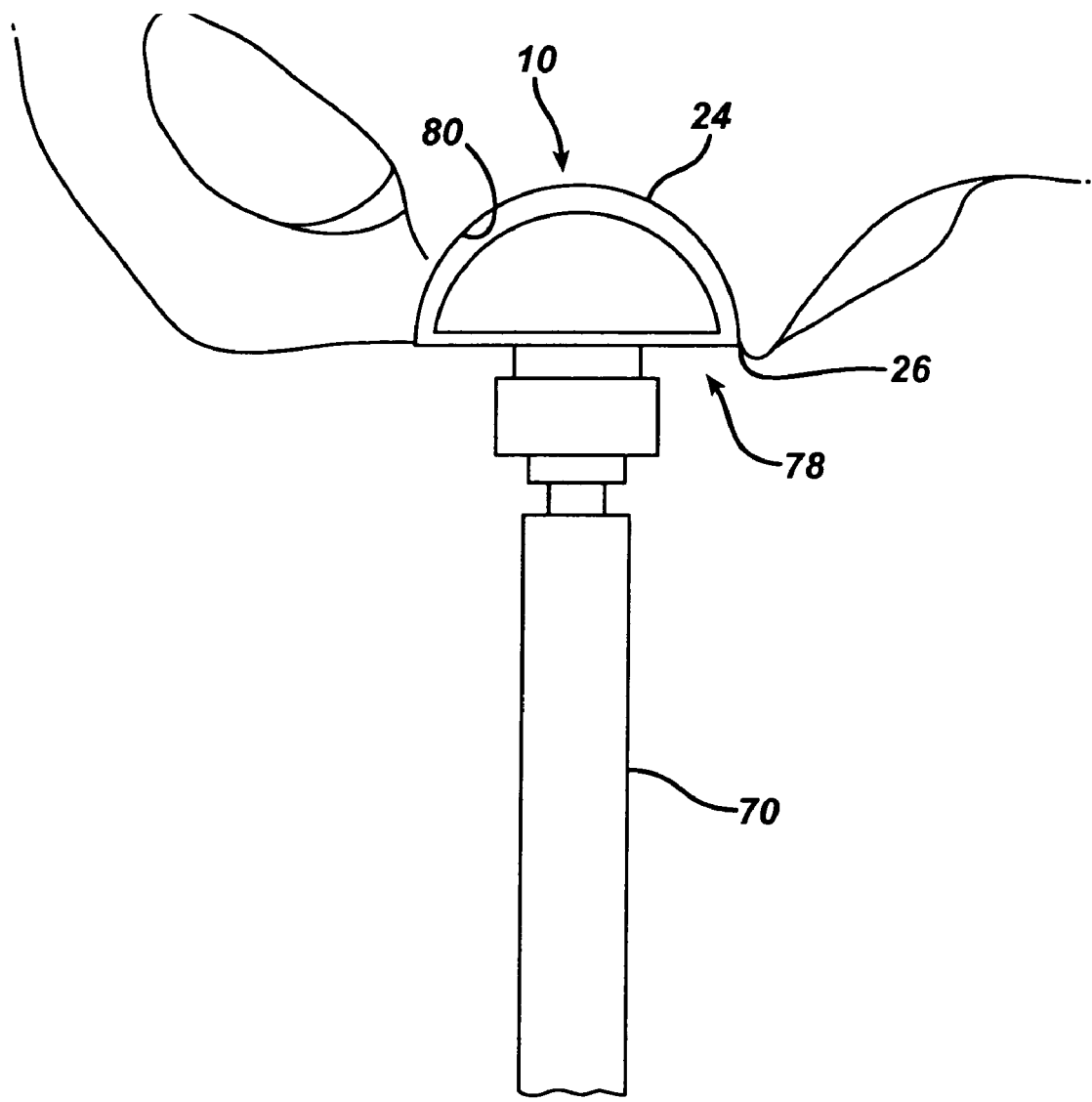
FIG. 7 is a partial plan view of the acetabular reamer and reamer driver assembly of FIG. 6 in position against the acetabulum of a patient.

Referring now to FIG. 7, the driver 70 is shown in position with the reamer 10 attached and in position in cavity 78 of the acetabulum 26. The cutter 24 of the reamer 10 is utilized to prepare the seat 80 in the acetabulum 26 for a hip cup implant (see FIG. 9).

Figure 8:
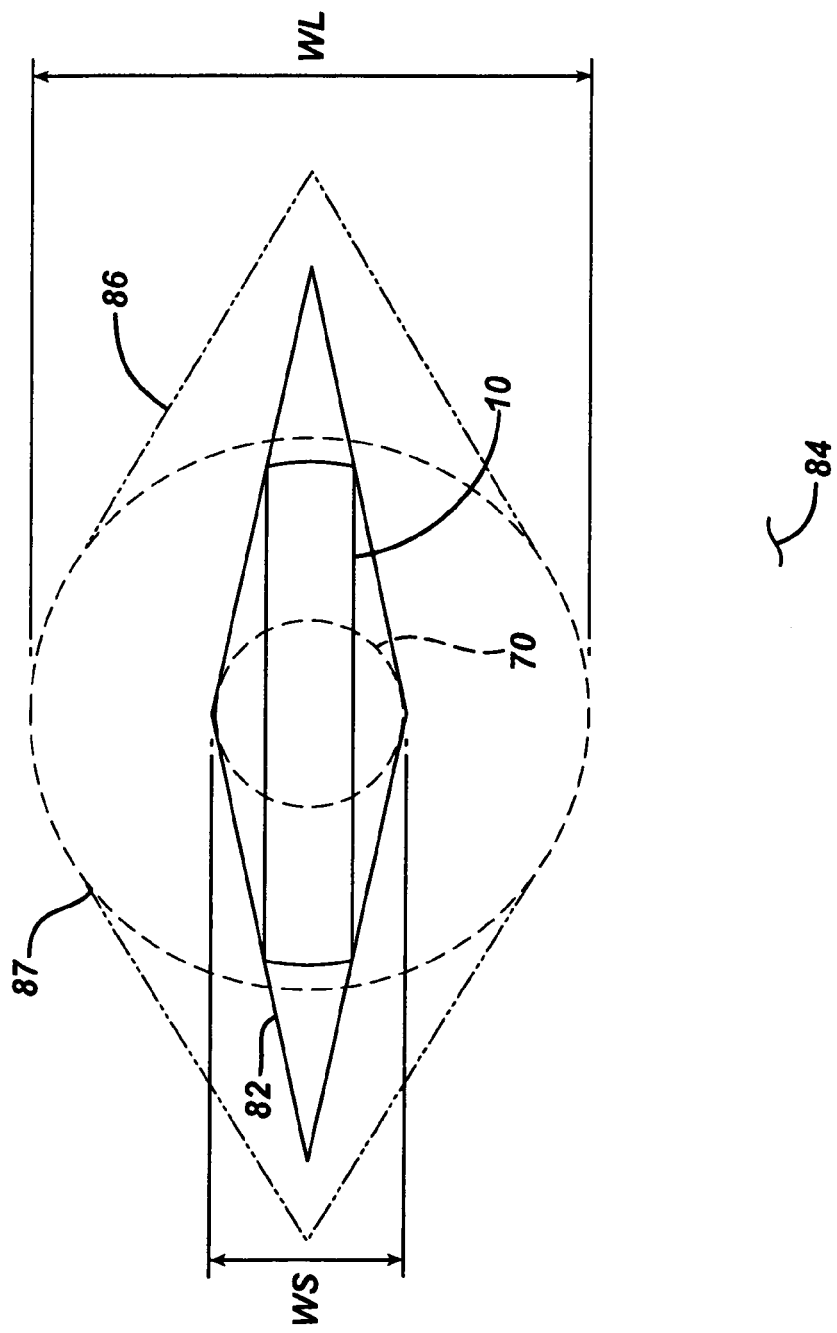
FIG. 8 is a partial plan view of an incision in a patient necessary for use with the use of the reamer in FIG. 1.

Referring now to FIG. 8, an incision 82 is shown in patient 84 for receiving the reamer 10 and the driver 70 to perform a minimally invasive procedure according to the present invention. For comparison an open procedure incision 86 is shown in phantom with a traditional acetabular reamer 87 also shown in phantom. It should be appreciated that the minimally invasive incision 82 has a width WS which is significantly smaller then the width WL of the open procedure incision 86. It should be appreciated that the minimally invasive incision 82 may disturb much less soft tissue such as ligaments, tendons, and fatty tissues than the open procedure incision 86.

Figure 9:
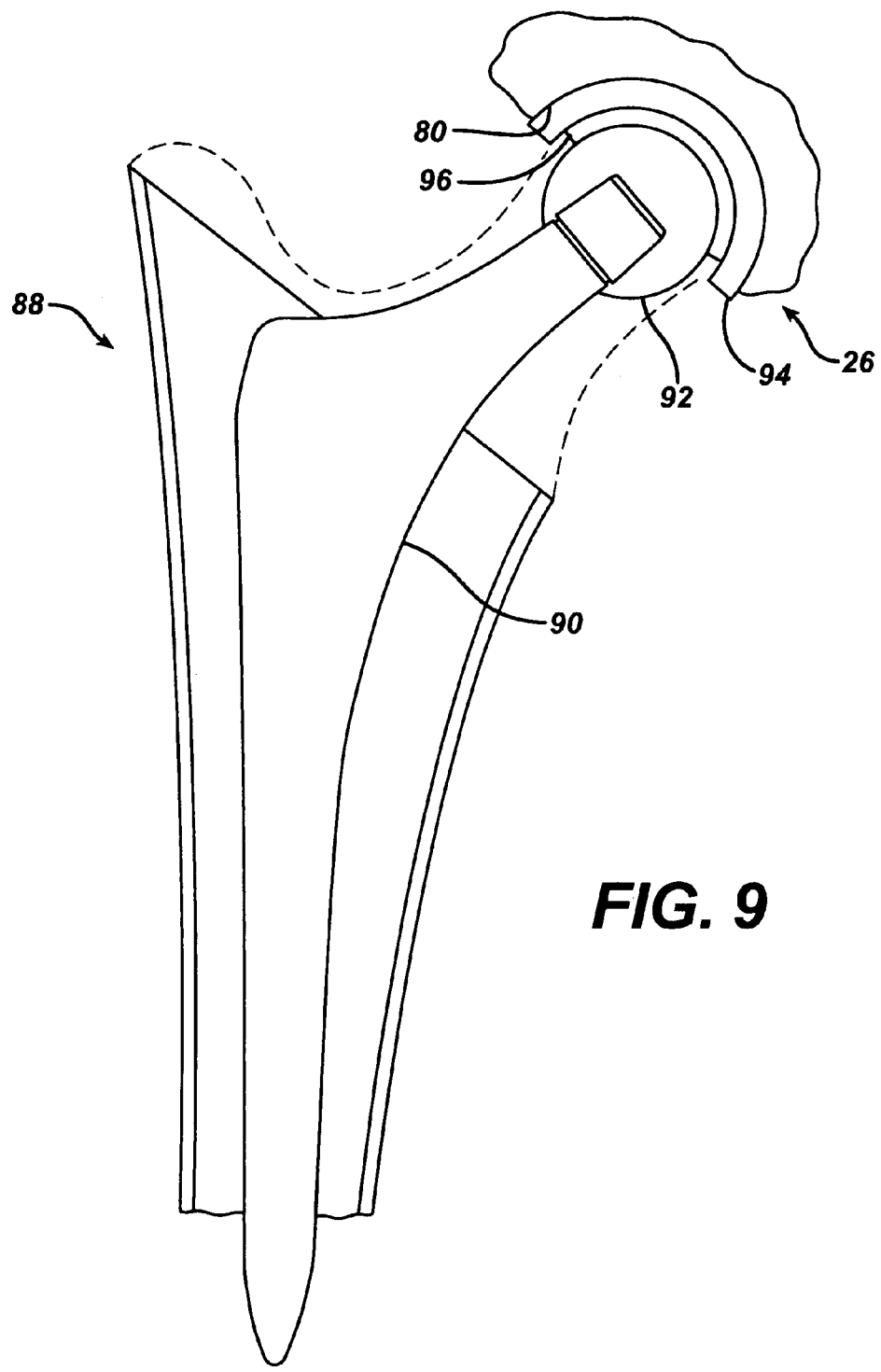
FIG. 9 is a partial plan view of hip prosthesis in position on an acetabulum that may be prepared by the acetabular reamer of the present invention.

Referring now to FIG. 9, a prosthesis 88 is shown for use with acetabular reamer 10 of the present invention. The hip construct 88 includes a hip stem 90 to which a head 92 is secured. The head 92 serves to replace the head of the femur. A hip cup 94 is positioned in the prepared surface 80 of the acetabulum 26. The hip cup 94 may be a unitary component that may be fitted to the head 92. Alternatively, a liner for example, a polymer, metal, or ceramic liner 96 may be positioned between the hip cup 94 and the head 92.

Figure 10:
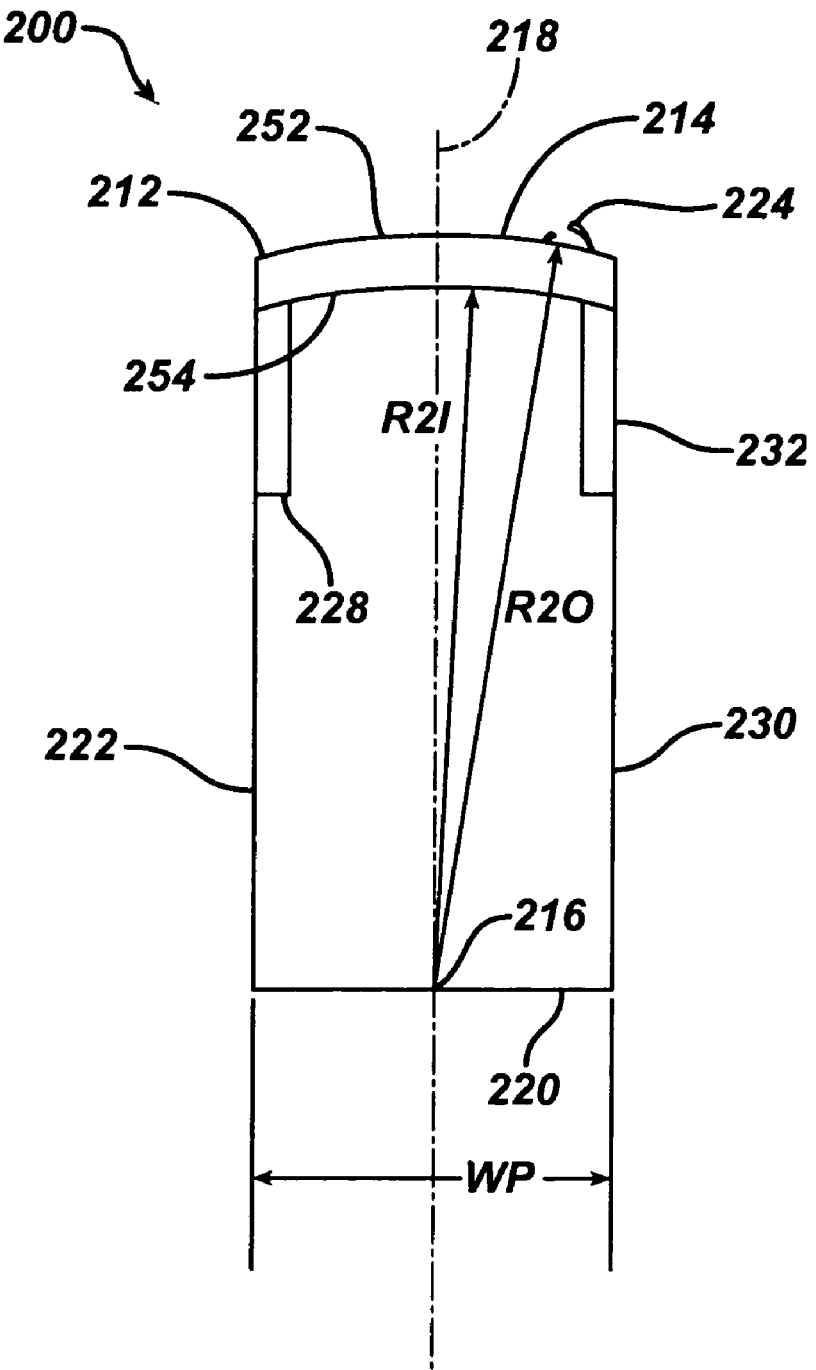
FIG. 10 is a partial cross sectional view of an acetabular reamer in accordance with yet another embodiment of the present invention having parallel relief surfaces.

Referring now to FIG. 10, an alternative embodiment of the present invention is shown as acetabular reamer 200. Acetabular reamer 200 is shown in FIG. 10 is similar to the acetabular reamer 10 of FIG. 1-5 and includes an arcuate plate 252 including peripheral surface 214 defined by radius R20 extending from origin 216 and inner arcuate surface 254 defined by radius R2I extending from origin 216. A cutter 224 is secured to the arcuate plate 252 and preferably a plurality of cutters 224 are uniformly dispersed along the peripheral surface of 214 of the plate 252.

Reamer 200, similarly to the reamer 10 in FIGS. 1-5 may include support structures for example, first support structure 228 extending along the first relief surface 222 of the body 212 inwardly from the inner arcuate surface 254 of the plate 252 toward the end surface 220. Similarly, the reamer 200 may include a second support structure 232 similarly extending inwardly from inner arcuate surface 254 of the plate 252.

The acetabular reamer 200 includes the first relief surface 222. The first relief surface as shown in FIG. 10 is preferably parallel and spaced from the axis of rotation 218 of the reamer 200. As shown in FIG. 10, the reamer 200 further includes a second relief surface 230 of the body 212, which is likewise generally planar and spaced from and parallel to the first relief surface 222 of the body 212. The first relief surface 222 and the second relief surface 230 define a width dimension WP there between. The width WP may be, for example, substantially smaller than twice the radius R20 of the body 212.

Figure 11:
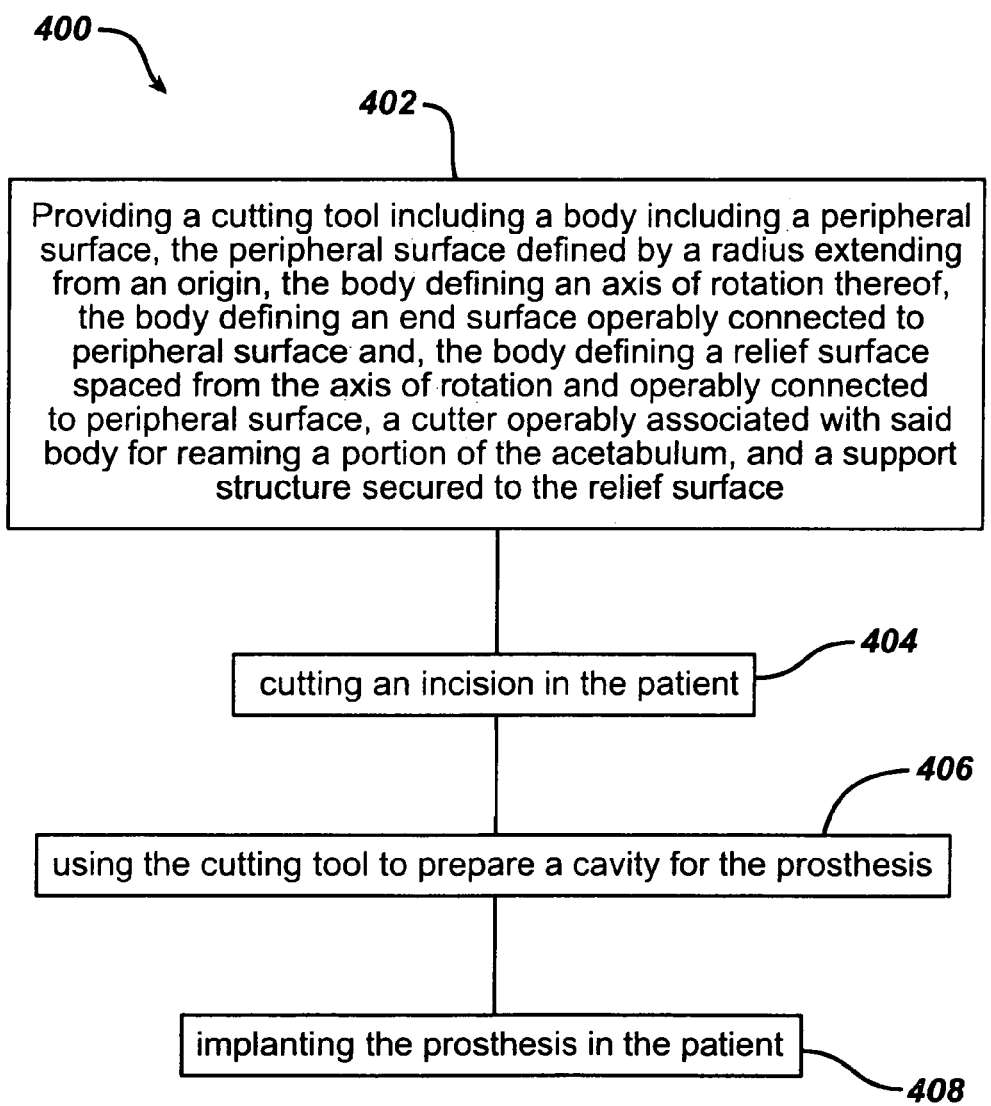
FIG. 11 is a flow chart of a method for performing arthroplasty utilizing the reamer of the present invention in accordance with an embodiment of the present invention.

Referring now to FIG. 11, an alternative embodiment of the present invention is shown as method 400 for implanting a prosthesis to perform joint arthroplasty on a patient. The method includes a step 402 of providing a cutting tool including a body including a peripheral surface. The peripheral surface is defined by a radius extending from an origin. The body defines an axis of rotation of the body. The body also defines an end surface operably connected to peripheral surface and a relief surface spaced from the axis of rotation and operably connected to peripheral surface. The cutting tool also includes a cutter operably associated with the body for reaming a portion of the acetabulum and a support structure secured to the relief surface. The method also includes step 404 of cutting an incision in the patient and step 406 of using the cutting tool to prepare a cavity for the prosthesis. The method further includes step 408 of implanting the prosthesis in the patient.

Although the present invention and its advantages have been described in detail, it should be understood that various changes, substitutions, and alterations can be made therein without departing from the spirit and scope of the present invention as defined by the appended claims.

We claim:

1. An acetabular reamer comprising:
   a body including a peripheral surface, the peripheral surface defined by a radius extending from an origin, said body defining an axis of rotation thereof, said body defining two end surfaces operably connected to peripheral surface and, said body defining first and second relief surfaces spaced from one another and the axis of rotation and operably connected to the peripheral surface, wherein the peripheral surface is a truncated hemisphere, the truncated hemisphere being defined by the two end surfaces and the first and second relief surfaces;
   a cutter operably associated with said body for reaming a portion of the acetabulum;
   a driver connector directly coupled to the end surface; and
   first and second support structures which are secured to and extend along the first and second relief surface respectively between opposite ends thereof at the intersections of the relief surfaces and the end surface, the support structures extending inwardly from the relief surfaces towards the origin.

2. The acetabular reamer of claim 1, wherein the end surface of said body is generally planar and perpendicular to the axis of rotation of said body.

3. The acetabular reamer of claim 1, wherein said cutter and said body are integral with each other.

4. The acetabular reamer of claim 1, wherein said body has a general form of a hollow, truncated hemisphere.

5. The acetabular reamer of claim 1, wherein the relief surface of said body is generally planar.

6. The acetabular reamer of claim 1, wherein the relief surface of said body is generally planar and parallel to the axis of rotation of said body.

7. The acetabular reamer of claim 1:
   wherein the first mentioned relief surface of said body is generally planar and parallel to the axis of rotation of said body; and
   wherein the second relief surface of said body is generally planar, spaced from, and generally parallel to the first mentioned relief surface of said body, the first mentioned relief surface and the second relief surface defining a width dimension therebetween, the width dimension being substantially smaller than twice the radius of said body.

8. The acetabular reamer of claim 7, further comprising a third support structure of said body, secured to the second support structure and to the first mentioned support structure for interconnecting the second support structure and to the first mentioned support structure.

9. The acetabular reamer of claim 7, wherein the width dimension is less than ⅔ of the radius of the body.

10. The acetabular reamer of claim 1:
    wherein the first mentioned relief surface of said body is generally planar; and
    wherein the second relief surface of said body is generally planar and spaced from the first mentioned relief surface, the first mentioned relief surface and the second relief surface defining an included angle therebetween.

11. The acetabular reamer of claim 10, wherein the included angle is less than 90 degrees.

12. The acetabular reamer of claim 1, further comprising a driver extending from said support structure.

13. The acetabular reamer of claim 1, wherein said support structure is integral with said body.

14. The acetabular reamer of claim 1, wherein said support structure comprises one of a rib, a gusset, a bar, a tube and a plate.

15. The acetabular reamer of claim 1, wherein said support structure extends substantially along the relief surface of said body.

16. An acetabular reamer comprising:
    a body including a peripheral surface, the peripheral surface of said body defined by a radius extending from an origin, said body defining an axis of rotation thereof, said body defining two generally planar end surfaces operably connected to peripheral surface of said body, said end surface being approximately perpendicular to the axis of rotation of said body, said body defining a generally planar first relief surface spaced from the axis of rotation and operably connected to peripheral surface, and, said body defining a generally planar second relief surface spaced from the axis of rotation of said body and from the first relief surface, the second relief surface operably connected to peripheral surface of said body, wherein the peripheral surface is a truncated hemisphere, the truncated hemisphere being defined by the two end surfaces and the first and second relief surfaces;
    a cutter operably associated with said body for reaming a portion of the acetabulum;
    a driver connector directly coupled to the end surface;
    a first support structure secured to the first relief surface; and
    a second support structure, secured to the second relief surface; wherein first and second support structures are secured to and extend along the first and second relief surface respectively between opposite ends thereof at the intersections of the relief surfaces and the end surface, the support structures extending inwardly from the relief surfaces towards the origin and wherein both the first support structure and second support structure are spaced from the driver connector.

17. The acetabular reamer of claim 16, wherein said cutter and said body are integral with each other.

18. The acetabular reamer of claim 16, wherein the first relief surface of said body and the second relief surface of said body are generally parallel to the axis of rotation of said body, the second relief surface of said body being generally parallel to the first relief surface, the first relief surface and the second relief surface defining a width dimension therebetween, the width dimension being smaller that the radius of said body.

19. The acetabular reamer of claim 18, wherein the first relief surface and the second relief surface define an included angle therebetween.

20. The acetabular reamer of claim 19, wherein the included angle is less than 90 degrees.

21. The acetabular reamer of claim 18, wherein the width dimension is less than ⅔ of the radius of the body.

22. The acetabular reamer of claim 16, further comprising a third support structure, secured to the second support structure and to the first support structure for interconnecting the second support structure and to the first support structure.

23. The acetabular reamer of claim 16, further comprising a driver extending from said support structure.

24. The acetabular reamer of claim 16, wherein at least one of said first support structure and said second support structure is integral with said body.

25. The acetabular reamer of claim 16, wherein at least one of said first support structure and said second support structure comprises one of a rib, a gusset, a bar, a tube and a plate.

26. The acetabular reamer of claim 16, wherein at least one of said first support structure and said second support structure extends substantially along the relief surface.

27. A rotatable tool for preparing a surface of a bone for implantation of a prosthesis for use in arthroplasty, said tool comprising:
  a body including a peripheral surface, the peripheral surface defined by a radius extending from an origin, said body defining an axis of rotation thereof, said body defining two end surfaces operably connected to peripheral surface and, said body defining first and second relief surfaces spaced from one another and the axis of rotation and operably connected to the peripheral surface, wherein the peripheral surface is a truncated hemisphere, the truncated hemisphere being defined by the two end surfaces and the first and second relief surfaces;
  a cutter operably associated with said body for reaming a portion of the acetabulum;
  a driver connector directly coupled to the end surface; and
  first and second support structures which are secured to and extend along the first and second relief surface respectively between opposite ends thereof at the intersections of the relief surfaces and the end surface, the support structures extending inwardly from the relief surfaces towards the origin.

28. The rotatable tool of claim 27:
  wherein the first mentioned relief surface of said body is generally planar and parallel to the axis of rotation of said body; and
  wherein the second relief surface is generally planar, spaced from, and generally parallel to the first mentioned relief surface, the first mentioned relief surface and the second relief surface defining a width dimension therebetween, the width dimension being substantially smaller that twice the radius of said body.

29. The rotatable tool of claim 27:
  wherein the first mentioned relief surface of said body is generally planar; and
  wherein the second relief surface is generally planar and spaced from the first mentioned relief surface, the first mentioned relief surface and the second relief surface defining an included angle therebetween.

30. The rotatable tool of claim 29, wherein the included angle is less than 90 degrees.

31. A method for implanting a prosthesis to perform joint arthroplasty on a patient, comprising:
  utilizing a cutting tool including a body including a peripheral surface, the peripheral surface defined by a radius extending from an origin, the body defining an axis of rotation thereof, the body defining two end surfaces operably connected to peripheral surface and, the body defining first and second relief surfaces spaced from one another and the axis of rotation and operably connected to the peripheral surface, wherein the peripheral surface is a truncated hemisphere, the truncated hemisphere being defined by the two end surfaces and the first and second relief surfaces a cutter operably associated with said body for reaming a portion of the acetabulum, a driver connector directly coupled to the end surface, and first and second support structures which are secured to and extend along the first and second relief surface respectively between opposite ends thereof at the intersections of the relief surfaces and the end surface, the support structures extending inwardly from the relief surfaces towards the origin;
  cutting an incision in the patient;
  using the cutting tool to prepare a cavity for the prosthesis; and
  implanting the prosthesis in the patient.

* * * * *